(12) United States Patent
Kim et al.

(10) Patent No.: US 10,037,616 B2
(45) Date of Patent: Jul. 31, 2018

(54) APPARATUS AND METHOD FOR RECONSTRUCTING IMAGE USING MICROWAVE

(71) Applicant: ELECTRONICS AND TELECOMMUNICATIONS RESEARCH INSTITUTE, Daejeon (KR)

(72) Inventors: Bo Ra Kim, Daejeon (KR); Seong Ho Son, Daejeon (KR); Simonov Nikolai, Daejeon (KR); Soon Ik Jeon, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 114 days.

(21) Appl. No.: 15/249,582

(22) Filed: Aug. 29, 2016

(65) Prior Publication Data
US 2017/0140559 A1 May 18, 2017

(30) Foreign Application Priority Data

Nov. 18, 2015 (KR) .................. 10-2015-0161899

(51) Int. Cl.
*G06T 11/00* (2006.01)
*A61B 5/05* (2006.01)

(52) U.S. Cl.
CPC .......... *G06T 11/005* (2013.01); *A61B 5/0507* (2013.01); *G06T 2207/10072* (2013.01); *G06T 2207/30068* (2013.01)

(58) Field of Classification Search
CPC .... G06T 11/003; G06T 11/005; G06T 11/006; G06T 2207/10072; G06T 2207/30068; A61B 5/0507; G01N 22/00
See application file for complete search history.

(56) References Cited

U.S. PATENT DOCUMENTS

| | | | |
|---|---|---|---|
| 7,825,667 B2 | 11/2010 | Fang et al. | 324/637 |
| 2006/0183995 A1* | 8/2006 | Bond et al. | 600/407 |
| 2011/0130656 A1 | 6/2011 | Son et al. | 600/430 |
| 2011/0227586 A1* | 9/2011 | Lovetri et al. | 324/637 |
| 2012/0163727 A1 | 6/2012 | Jeon et al. | 382/254 |
| 2013/0135450 A1* | 5/2013 | Pallone et al. | H04N 13/0221 348/50 |
| 2013/0204118 A1* | 8/2013 | Golnabi et al. | A61B 5/0035 600/411 |

FOREIGN PATENT DOCUMENTS

| | | | | |
|---|---|---|---|---|
| KR | 10-2010-0066270 A | 6/2010 | ............... | A61B 5/00 |
| KR | 10-2013-0010156 A | 1/2013 | ............... | G01N 29/00 |
| KR | 10-2015-0018222 A | 2/2015 | ............... | G06T 1/00 |

* cited by examiner

*Primary Examiner* — Andrew W Johns
(74) *Attorney, Agent, or Firm* — NSIP Law

(57) ABSTRACT

Provided is an apparatus for reconstructing an image using a microwave. The apparatus includes: a microwave measurement unit configured to obtain a microwave measurement value for a microwave measurement object; and an image reconstruction unit configured to perform an image reconstruction by using the microwave measurement value and shape boundary information of the object.

17 Claims, 7 Drawing Sheets

APPARATUS AND METHOD FOR RECONSTRUCTING IMAGE USING MICROWAVE

CROSS-REFERENCE TO RELATED APPLICATION

This application claims the benefit of priority to Korean Patent Application No. 10-2015-0161899, filed on Nov. 18, 2015 in the Korean Intellectual Property Office, the disclosure of which is incorporated herein in its entirety by reference.

BACKGROUND OF THE INVENTION

Field of the Invention

The present disclosure relates to an apparatus and a method for reconstructing an image using a microwave, and more particularly, to a technology for reconstructing an image of a cross-section photographed signal obtained by photographing a cross section using a microwave.

Description of the Related Art

It is the most generally used method for an early diagnosis of cancer to detect a heterogeneous tissue through a mechanical examination. Such a mechanical examination method has an advantage in that the test process is relatively simple. However, since the diagnostic success rate is extremely slim, it is accomplished in parallel with a secondary diagnosis method such as a biopsy. Thus, a method for diagnosing a cancer through more accurate mechanical examination is required.

Thus, as a technology for an accurate diagnosis of cancer, a technology of photographing the object (breast) by using a propagation characteristic of a radio frequency (RF) microwave signal having a 500 MHz~3000 MHz frequency, which is an example of the microwave, and linearly outputting the photographed image in order that user is able to recognize the photographed image is suggested.

In detail, in a conventional microwave cross-section photographing, the general image output method generates a specific image reconstruction data value which is a data value for outputting an image output data value, by sensing and measuring a microwave to process a signal and reconstructing the image. In addition, based on the generated specific image reconstruction data value, the image is outputted linearly without change so that user is able to recognize the image.

That is, a conventional microwave tomography may have a monopole antenna, which is placed in a circle, that can transmit and receive a certain microwave into a tank filled up with a microwave matching solution, and the monopole antenna accomplishes the three-dimensional microwave measurements on the subject breast exists in the tank.

Such a conventional microwave tomography photographs a cross-section by using the microwave and collects the strength of each microwave from one section (e.g., cross-section) on a space in which the microwaves progress, and reconstructs a distribution image of electrical characteristics of the materials in the space through a calculation of the collected data to display on a monitor or the like.

That is, the conventional microwave tomography measures the microwave transmitted in the space, and obtains a photographed image of a cross section by reconstructing the image using a microwave value of the measured microwave.

Various numerical analysis methods using an algorithm for such an image reconstruction are used. However, since the amount of computation is large as the conventional numerical analysis method is used to implement the image reconstruction without limitation, the computation time is increased.

SUMMARY OF THE INVENTION

The present disclosure has been made in view of the above problems, and provides an apparatus and a method for reconstructing an image using a microwave, which are capable of reducing the amount of calculations for an image reconstruction area and improving the accuracy by reconstructing an image by using shape boundary information obtained from a shape boundary measuring device when reconstructing the image using a microwave.

The present disclosure further provides an apparatus and a method for reconstructing an image using a microwave, which are capable of improving an operation speed by using a high-speed operation parallel method when reconstructing an image using a microwave.

In accordance with an aspect of the present disclosure, an apparatus for reconstructing an image using a microwave includes: a microwave measurement unit configured to obtain a microwave measurement value for a microwave measurement object; and an image reconstruction unit configured to perform an image reconstruction by using the microwave measurement value and shape boundary information of the object. The apparatus further includes a shape measurement unit configured to obtain the shape boundary information of the object. The image reconstruction unit receives the shape boundary information from a user. The image reconstruction unit includes: an image restoring unit configured to form an image reconstruction area mesh by using the microwave measuring value, and set an outer boundary line to the image reconstruction area mesh by using the shape boundary information of the object to perform the image reconstruction; and a high-speed operation parallel processing unit configured to calculate a microwave for an image reconstruction area so as to perform the image reconstruction, and calculate an error between the calculated microwave value and the microwave measurement value to provide to the image restoring unit. The image restoring unit sets a mesh to the image reconstruction area in an interior of the outer boundary line, and performs the image reconstruction with respect to the mesh of an interior of the outer boundary line by removing the mesh of an exterior of the outer boundary line. The image restoring unit sets an initial distribution of electrical characteristics to the mesh within the image reconstruction area, and changes a distribution of electrical characteristics of the mesh depending on the error. The image restoring unit outputs a restored image at the image reconstruction area when the error satisfies a preset range, and performs again the image reconstruction after changing the distribution of electrical characteristics within the mesh when the error does not satisfy the preset range. The image restoring unit changes the distribution of electrical characteristics of the mesh of the interior of the outer boundary line and maintains the initial distribution of electrical characteristics of the mesh of the exterior of the outer boundary line. The microwave measurement unit transmits a difference value between a primary microwave measurement value measured in a state where the object is not inserted and a secondary microwave measurement value measured in a state where the object is inserted to the image reconstruction unit, as the microwave measurement value.

In accordance with another aspect of the present disclosure, a method for reconstructing an image using a microwave includes: receiving a microwave measurement value and shape boundary information of a microwave measurement object; and performing an image reconstruction by using the microwave measurement value and the shape boundary information. Receiving a microwave measurement value and shape boundary information includes receiving the shape boundary information from a user or a shape measurement unit measured the shape boundary information of the object. Performing an image reconstruction includes: setting a mesh for the image reconstruction area by using the microwave measurement value; setting an outer boundary line to the image reconstruction area by using the shape boundary information; and obtaining an microwave calculation value by calculating the microwave after setting an initial distribution for electrical characteristics to the mesh. The method further includes calculating an error between the microwave measurement value and the microwave calculation value. The method further includes: outputting the restored image when the error satisfies a preset range; and performing again the image reconstruction by changing the distribution of electrical characteristics of the mesh when the error does not satisfy the preset range. Performing again the image reconstruction includes maintaining the initial distribution of electrical characteristics for the mesh of the exterior of the outer boundary line and changing the distribution of electrical characteristics for the mesh of the interior of the outer boundary line. Setting an outer boundary line to the image reconstruction area includes leaving the mesh of the interior of the outer boundary line and removing the mesh of the exterior of the outer boundary line. Obtaining an microwave calculation value includes calculating the microwave by performing a high-speed parallel operation.

BRIEF DESCRIPTION OF THE DRAWINGS

The objects, features and advantages of the present disclosure will be more apparent from the following detailed description in conjunction with the accompanying drawings, in which.

DETAILED DESCRIPTION OF EXEMPLARY EMBODIMENTS

Exemplary embodiments of the present disclosure are described with reference to the accompanying drawings in detail. The same reference numbers are used throughout the drawings to refer to the same or like parts. Detailed descriptions of well-known functions and structures incorporated herein may be omitted to avoid obscuring the subject matter of the present disclosure.

Hereinafter, embodiments of the present disclosure are described with reference to FIG. 1 to FIG. 7.

Figure 1:
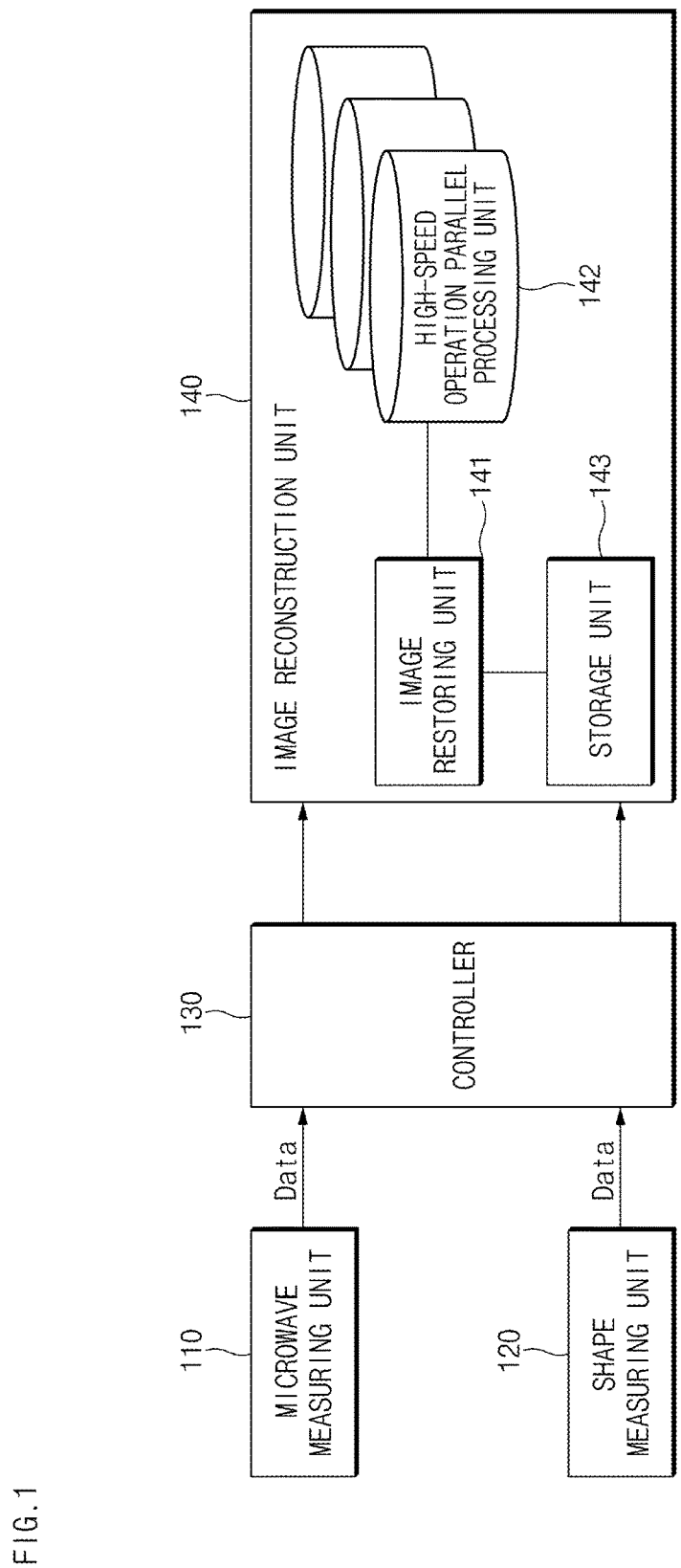
FIG. 1 is a diagram illustrating a configuration of an apparatus for reconstructing an image according to an embodiment of the present disclosure.

FIG. 1 is a diagram illustrating a configuration of an apparatus for reconstructing an image according to an embodiment of the present disclosure.

The apparatus for reconstructing an image according to an embodiment of the present disclosure may include a microwave measuring unit 110, a shape measuring unit 120, a controller 130, an image reconstruction unit 140.

The microwave measuring unit 110 may measure the microwave of an object. As a microwave measurement value, a difference value between a primary microwave measurement value measured in a state where the object (breast) is not inserted and a secondary microwave measurement value measured in a state where the object (breast) is inserted may be transmitted to the image reconstruction unit 140.

The shape measuring unit 120 may measure shape boundary information which is information on a boundary surface (boundary line) of the outer shape of the object (breast, or the like).

The controller 130 may control the overall operation of the microwave measuring unit 110, the shape measuring unit 120, and the image reconstruction unit 140.

The image reconstruction unit 140 may output an reconstructed image by performing an image reconstruction using an microwave measurement value and the shape boundary information. To this end, the image reconstruction unit 140 may include an image restoring unit 141, a high-speed operation parallel processing unit 142, and a storage unit 143.

Figure 3:
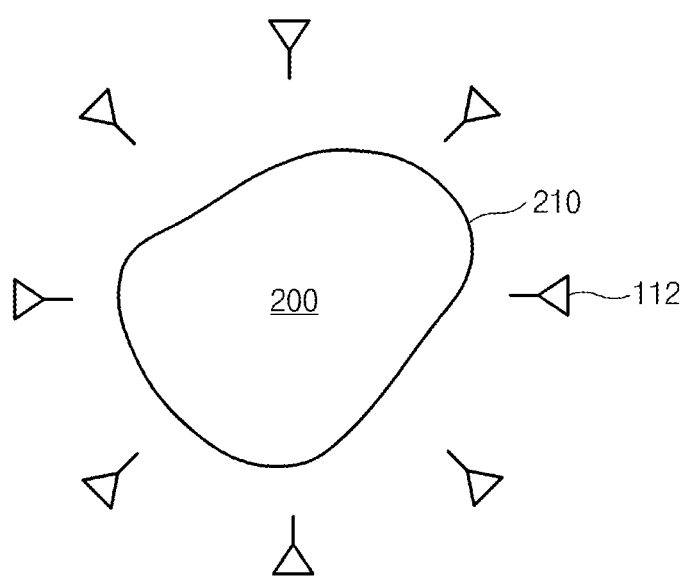
FIG. 3 is a cross-sectional diagram illustrating an interior of a tank set to an image reconstruction area according to an embodiment of the present disclosure.
Figure 4:
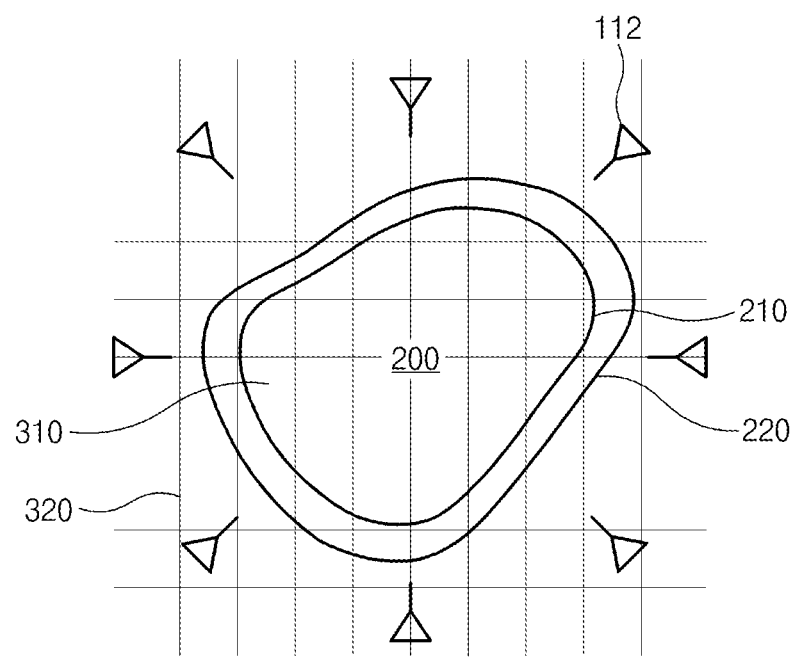
FIG. 4 is a diagram illustrating an example of a mesh formed in the image reconstruction area for the interior of a tank of FIG. 3.
Figure 5:
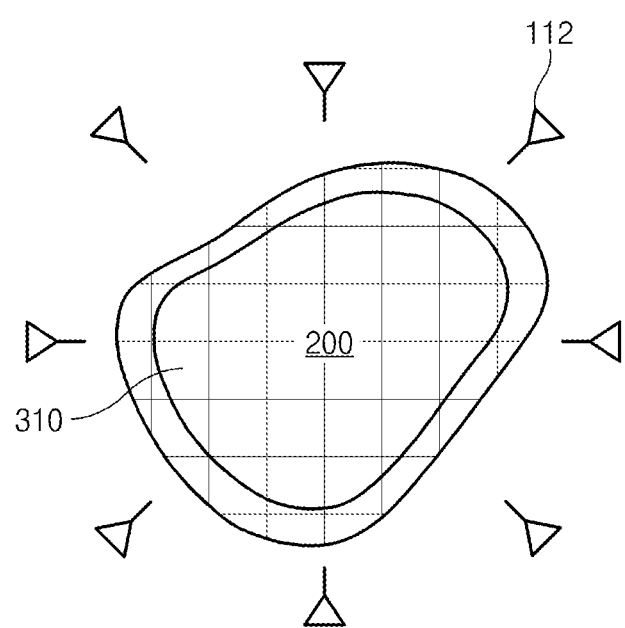
FIG. 5 is a diagram illustrating an example of a mesh set only within a shape boundary of object in the image reconstruction area for the interior of a tank of FIG. 4.

The image restoring unit 141 may form an image reconstruction area mesh as shown in FIG. 4 after reconstructing the image as shown in FIG. 3 by using a microwave measuring value, and set an outer boundary line 220 to the image reconstruction area mesh by using the shape boundary information of the object 200. The image restoring unit 141 may set the initial distribution of electrical characteristics to the mesh 310, 320 within the image reconstruction area, and change the distribution of electrical characteristics of the mesh 310 within the outer boundary line 220 depending on the error calculated by the high-speed operation parallel processing unit 142. The image restoring unit 141 may output a restored image at the image reconstruction area when the error calculated by the high-speed operation parallel processing unit 142 satisfies a preset range, and may perform again the image reconstruction after changing the distribution of electrical characteristics within the mesh 310 when the error calculated by the high-speed operation parallel processing unit 142 does not satisfy the preset range. At this time, the image restoring unit 141 may change the distribution of electrical characteristics of the mesh 310 of the interior of the outer boundary line 220 and may maintain the initial distribution of electrical characteristics of the mesh 320 of the exterior of the outer boundary line 220. In addition, the image restoring unit 141 may perform the image reconstruction only for the mesh of the interior of the outer boundary line 220 by setting a mesh to the image reconstruction area of the interior of the outer boundary line 220 as shown in FIG. 5 and removing the mesh of the exterior of the outer boundary line 220.

The high-speed operation parallel processing unit 142 may perform a forward direction analysis for the image reconstruction area to calculate the microwave and calculate an error between the calculated microwave value and the microwave measurement value received from the microwave measuring unit 110. At this time, the high-speed operation parallel processing unit 142 may reduce the calculation amount and the calculation time by performing a high-speed operation in parallel during the microwave calculation and the error calculation.

The storage unit 143 may store information such a microwave measurement value, boundary shape information, a microwave calculation value, an initial distribution of electrical characteristics, and a changed electrical characteristics distribution.

Figure 2:
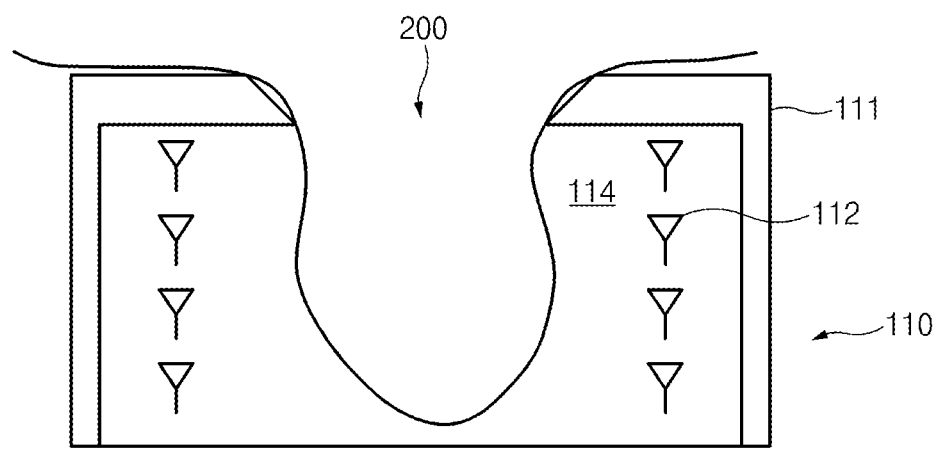
FIG. 2 is a diagram illustrating an example of a case where an object is inserted into a tank of an apparatus for reconstructing an image according to an embodiment of the present disclosure.

Thus, the present disclosure may reduce the calculation amount and the calculation time and obtain an accurate image restoration result during the image reconstruction by using the shape boundary information of the object. Additionally, the calculation amount and the calculation time may be further reduced through the high-speed operation parallel processing unit. FIG. 2 is a diagram illustrating an example of a case where an object is inserted into a tank of an apparatus for reconstructing an image according to an embodiment of the present disclosure.

The tank 111 of the microwave measuring unit 110 may be filled with the matching solution 114, and a plurality of transmission and reception antennas 112 are arranged in the tank 111.

In the microwave measuring unit 110, when one of the transmission and reception antennas 112 transmits a microwave before the object 200 such as a breast is inserted into the tank 111, the remaining transmission and reception antennas may receive and primarily measure the microwave. Then, when one of the transmission and reception antennas 112 of the microwave measuring unit 110 transmits the microwave in a state where the object 200 is inserted into the tank 111, the remaining transmission and reception antennas may receive the microwave which passed through the object to secondarily measure the microwave. Therefore, the microwave measuring unit 110 may obtain a difference value between the primary measurement value and the secondary measurement value from a final microwave measurement value and provide the difference value to the image reconstruction unit 140 through the controller 130. At this time, the cross-section of the object 200 which is measured in the state where the object is inserted into the tank 111 is shown in FIG. 3. Referring to FIG. 3, the transmission and reception antenna 112 which can transmit and receive a microwave may be located around the object 200.

Figure 6:
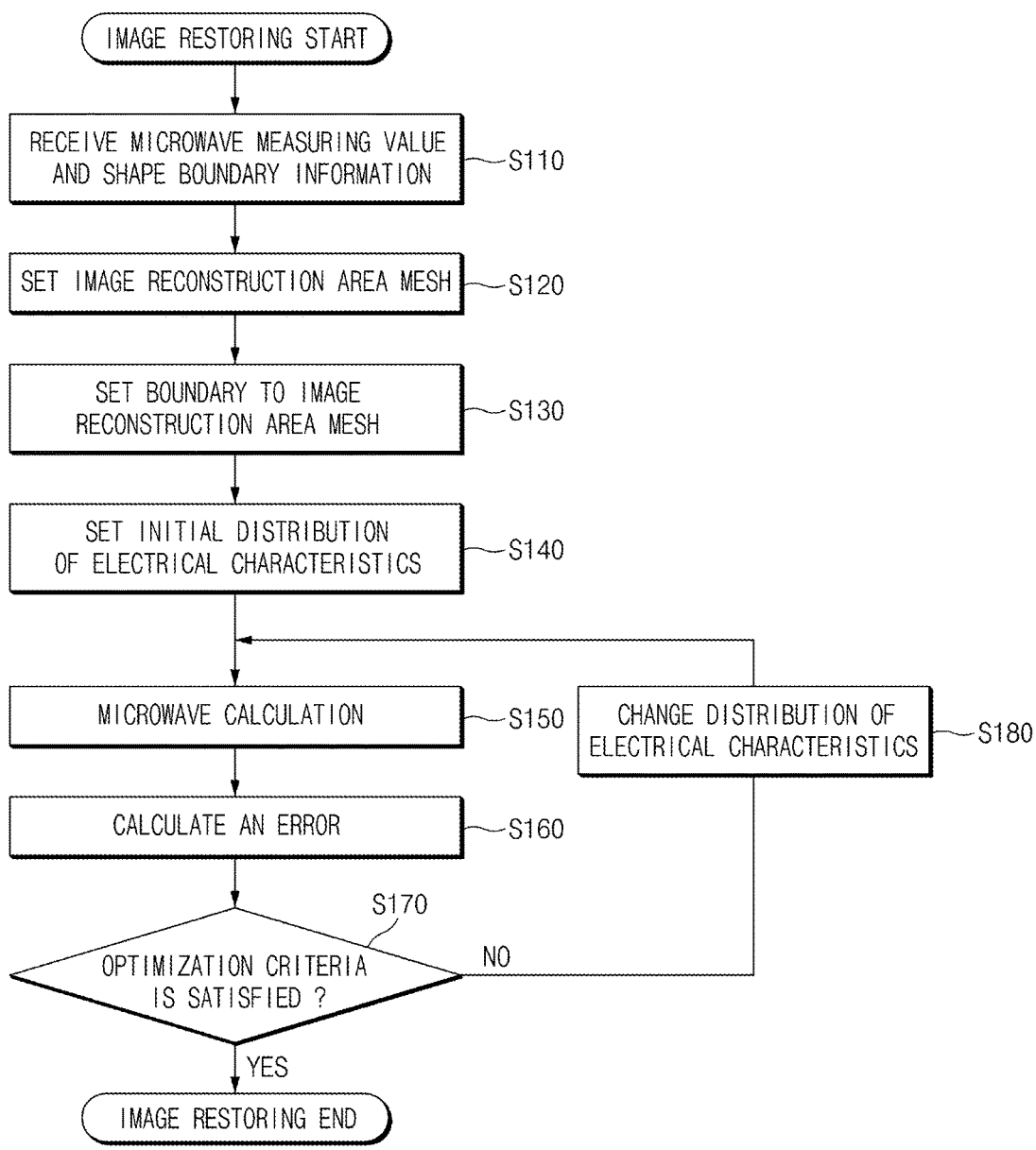
FIG. 6 is a flowchart illustrating a method for reconstructing an image using a microwave according to an embodiment of the present disclosure.

Hereinafter, the method for reconstructing an image according to an embodiment of the present disclosure is described in detail with reference to FIG. 6.

First, after obtaining a microwave measuring value which is a difference value between the primary measurement value obtained by primarily measuring the microwave by the microwave measuring unit 110 before the object 200 is inserted into the tank 111 and the secondary measurement value obtained by secondarily measuring the microwave by the microwave measuring unit 110 in the state where the object 200 is inserted into the tank 111, the microwave measuring unit 110 may transmit the microwave measuring value to the image reconstruction unit 140 through the controller 130.

In addition, the shape measuring unit 120 may measure the shape boundary of the object 200 in the state where the object 200 is inserted into the tank 111, and transmit the shape boundary information to the image reconstruction unit 140 through the controller 130.

Thus, the image reconstruction unit 140 may receive the microwave measuring value from the microwave measuring unit 110 and receive the shape boundary information from the shape measuring unit 120 (S110).

After forming the image reconstruction area for the interior of the tank 111 where a plurality of antennas 112 are disposed in a boundary surface 210 of the object 200 and the exterior of the boundary surface 210 by using the microwave measurement value as shown in FIG. 3, the image reconstruction unit 140 may set an image reconstruction area mesh (S120).

Then, the image reconstruction unit 140 may set the boundary by applying the shape boundary information into the image reconstruction area as shown in FIG. 4 (S130). Referring to FIG. 4 the image reconstruction unit 140 may form an outer boundary line 220 spaced apart at regular distance around the object 200 by using the shape boundary information received from the shape measuring unit 120. That is, since the outer boundary line 220 may be a shape boundary set by the shape boundary information and may include a little error in a real measurement, it may be set to be identical with or slightly larger than the size of the object. At this time, the present disclosure discloses an example of using the measured shape boundary information. However, a user may arbitrarily set a boundary of an object or the shape boundary information for restoring area from the user.

In addition, as shown in FIG. 5, the present disclosure may proceed with the image restoration by setting the mesh only within the object 200. In the case of FIG. 5, since the allocated number of the mesh is small, the calculation amount is significantly decreased such that the microwave calculation time and all operation time is shortened.

Then, the image reconstruction unit 140 may set the initial distribution of electrical characteristics to the mesh within the image reconstruction area (S140). That is, the image reconstruction unit 140 may arbitrarily set the initial distribution value of the permittivity and the conductivity which are the electrical characteristics for the state where the object 200 does not exist within the tank divide by the mesh.

In FIG. 4, the image reconstruction unit 140 may allocate the initial distribution of the different electrical characteristics to the mesh 310 of the interior of the outer boundary line 220 of the object 200 and the mesh 320 of the exterior of the outer boundary line 220 of the object 200. Since the user may know the condition of the exterior of the object 200 during the microwave measurement, the image reconstruction unit 140 may allocate the already known electrical characteristics to the mesh 320 of the exterior of the outer boundary line 220 of the object 200. In addition, the image reconstruction unit 140 may enable the mesh 310 of the interior of the outer boundary line 220 of the object 200 to arbitrarily receive the electrical characteristics of the breast from a program or a user.

The image reconstruction unit 140 may generate the microwave calculation value by performing the forward direction analysis for the image reconstruction area (S150). The image reconstruction unit 140 may calculate the microwave based on the distribution of electrical characteristics at the step S140. At this time, the image reconstructs unit 140 may perform the calculation of the microwave from the antenna 112 to each mesh and the calculation of the microwave from the mesh to each antenna by using the following Equation 1.

$$\text{Green's function} * \text{Basis function} * \text{Contrast} * \text{Total E-filed} = \text{Microwave calculation value} \quad [\text{Equation 1}]$$

Here, Green's function represents a Green's function relationship between the mesh 710 to 320 and the antenna 112, Basis function represents a basis function for each net, Contrast represents a difference of electrical characteristics between a background material and an interior material for each mesh, and Total E-filed represents a total electric field.

As shown in Equation 1, the image reconstruction unit 140 may calculate the microwave calculation value by performing an operation of Green's function, Basis function, Contrast, and Total E-filed.

At this time, the calculation time of the microwave calculation may be reduced by performing a high-speed operation processing in parallel through the high-speed operation parallel processing unit 142.

The image reconstruction unit 140 may calculate an error between the obtained measurement value and the generated microwave calculation value (S160). In this case, the calculation time of the error calculation may be reduced by performing a high-speed operation processing in parallel through the high-speed operation parallel processing unit 142.

The image reconstruction unit 140 may check whether the change of the calculated error satisfies a preset optimization criteria (S170).

When the preset optimization criteria is not satisfied, after changing the distribution (parameters) of electrical characteristics of the mesh (S180), the image reconstruction unit 140 may repeat the microwave calculation of the step S150 and the error calculation of the step S160.

At this time, during the change of the distribution of electrical characteristics, it is not necessary to change the distribution with respect to all meshes allocated to the interior of the tank by using the shape boundary information. It is enough to change the distribution of electrical characteristics of the mesh 310 of the interior of the outer boundary line 220 while maintaining the initially set condition in the mesh 320 of the exterior of the outer boundary line 220.

In this case, in the state where the shape boundary information does not exist, during the update under the condition of unknown electrical characteristics of all meshes, the calculation amount is large and the calculation time takes a long time, and it is difficult to obtain an accurate image as the microwave calculation value is influenced for all mesh. Thus, after setting the outer boundary line 220 by applying the shape boundary information, the present disclosure may change the distribution of electrical characteristics only in the mesh 310 of the interior based on the outer boundary line 220, thereby reducing the calculation amount and the calculation time and obtaining an accurate image.

Meanwhile, when the optimization criteria is satisfied, the image reconstruction unit 140 may terminate the image restoration, change the information generated by the calculation into graphic data and provide the restored image by displaying the image using a device such as a monitor.

In the related art, during the image reconstruction, since the calculation is accomplished on the assumption that electrical characteristics for all meshes dividing the interior of the tank is unknown, an inverse scattering calculation should be accomplished with respect to all meshes in the step of changing the distribution of electrical characteristics such that the calculation amount and the calculation time are increased. In addition, it is not easy to obtain an accurate value as it is affected by an inverse scattering calculation value in all unnecessary parts.

In order to solve this problem, the present disclosure may apply the shape boundary information in the step (S140) of initial distribution of electrical characteristics for mesh, and in the step (S180) of distribution change of electrical characteristics, thereby significantly reducing the calculation amount in the forward direction analysis and reverse direction analysis parts.

In addition, the present disclosure may accomplish the microwave calculation and the error calculation through the high-speed operation parallel processing unit 142.

Further, since the present disclosure restricts the image restoration area by using the shape boundary information, it does not consider the effect of the unnecessary neighboring area, thereby obtaining the accurate internal image.

Figure 7:
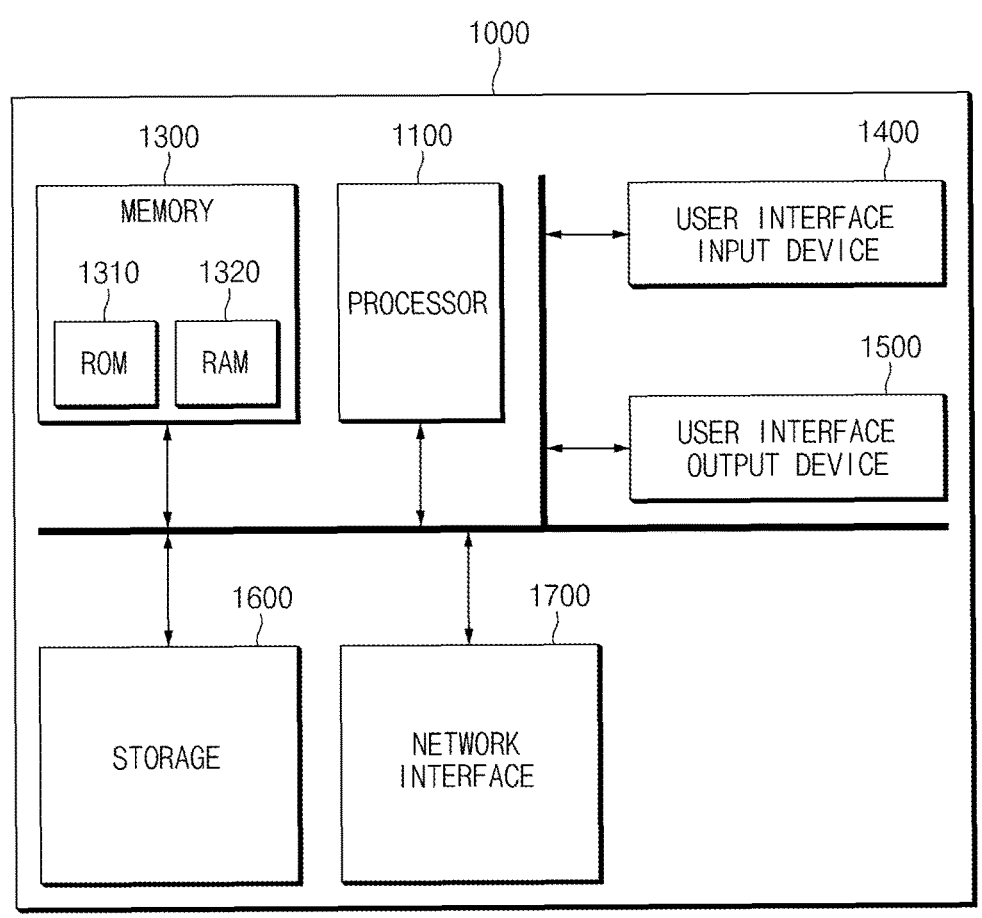
FIG. 7 is a diagram illustrating a configuration of a computing system implementing the method for reconstructing an image using a microwave according to an embodiment of the present disclosure.

FIG. 7 is a diagram illustrating a configuration of a computing system implementing the method for reconstructing an image using a microwave according to an embodiment of the present disclosure.

Referring to FIG. 7, the computing system 1000 may include at least one processor 1100 which is connected via a bus 1200, memory 1300, an user interface input device 1400, an user interface output device 1500, a storage 1600, and a network interface 1700.

The processor 1100 may be a semiconductor device for performing a processing for instructions stored in a central processing unit (CPU) or the memory 1300 and/or the storage 1600. The memory 1300 and the storage 1600 may include various types of volatile and nonvolatile storage media. For example, the memory 1300 may include a Read Only Memory (ROM) and Random Access Memory (RAM).

Thus, the steps of the method or the algorithm described in association with the embodiments disclosed herein may be directly implemented by a hardware, a software module, or a combination of the two executed by the processor 1100. The software module may reside in a storage medium (i.e., in the memory 1300 and/or the storage 1600) such as a RAM memory, a flash memory, a ROM memory, an EPROM memory, an EEPROM memory, a register, a hard disk, a removable disk, and CD-ROM. The exemplary storage medium may be coupled to the processor 1100, and the processor 1100 may read information from the storage medium and write information to the storage medium. Alternatively, the storage medium may be integrated in the processor 1100. The processor and the storage medium may reside in an application specific integrated circuit (ASIC). The ASIC may reside in a user terminal. Alternatively, the processor and the storage medium may reside in the user terminal as an individual component.

The present technology may reconstruct the image using the microwave by applying the boundary shape information, thereby significantly reducing the calculation amount in the forward direction analysis and reverse direction analysis parts and obtaining the accurate internal image as it does not consider the effect of the unnecessary neighboring area.

In addition, the present technology may accomplish the microwave calculation and the error calculation through the high-speed operation parallel processing unit 142, thereby significantly reducing the calculation time to reduce the image reconstruction time.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An apparatus for reconstructing an image using a microwave, the apparatus comprising:
a controller configured to control obtaining a microwave measurement value for a microwave measurement object based on a transmitted microwave; and
one or more processors configured to:
selectively, with respect to an interior of an outer boundary determined from shape boundary information of the object, change a distribution of electrical characteristics of an image reconstruction area mesh that is based on the microwave measurement value; and
perform an image reconstruction by using the selectively changed distribution of electrical characteristics of the image reconstruction area mesh.

2. The apparatus of claim 1, wherein the controller is further configured to control obtaining the shape boundary information of the object.

3. The apparatus of claim 1, wherein, to perform the image reconstruction, the one or more processors are configured to:
form the image reconstruction area mesh by using the microwave measuring value, and set an outer boundary line to the image reconstruction area mesh by using the shape boundary information of the object to perform the image reconstruction; and
through parallel processing, calculate a microwave for an image reconstruction area so as to perform the image reconstruction, and calculate an error between the calculated microwave value and the microwave measurement value.

4. The apparatus of claim 3, wherein the one or more processors are configured to
set a mesh portion, of the image reconstruction area mesh, of an interior of the outer boundary line, and
perform the image reconstruction with respect to the mesh portion of the interior by removing a mesh portion, of the image reconstruction area mesh, of an exterior of the outer boundary line.

5. The apparatus of claim 3, wherein the one or more processors are configured to
set an initial distribution of electrical characteristics to a mesh portion, of the image reconstruction area mesh, of an interior of the outer boundary line, and
changes a distribution of electrical characteristics of the mesh portion of the interior depending on the error.

6. The apparatus of claim 5, wherein the one or more processors are configured to
output a restored image at the image reconstruction area when the error satisfies a preset range, and
perform again the image reconstruction after changing the distribution of electrical characteristics of the mesh portion of the interior when the error does not satisfy the preset range.

7. The apparatus of claim 6, wherein the one or more processors are configured to
change the distribution of electrical characteristics of the mesh portion of the interior, and
maintain an initial distribution of electrical characteristics of a mesh portion, of the image reconstruction area mesh, of an exterior of the outer boundary line.

8. The apparatus of claim 1, wherein, for the controlling of the obtaining of the microwave measurement value, the controller controls obtaining a difference value between a primary microwave measurement value measured in a state where the object is not inserted in an image reconstruction space and a secondary microwave measurement value measured in a state where the object is inserted in the image reconstruction space, as the microwave measurement value.

9. An apparatus for reconstructing an image using a microwave, the apparatus comprising:
a controller configured to control obtaining a microwave measurement value for a microwave measurement object; and
one or more processors configured to perform an image reconstruction by using the obtained microwave measurement value and shape boundary information of the object,
wherein the one or more processors receive the shape boundary information from a user.

10. A method for reconstructing an image using a microwave, the method comprising:
obtaining a microwave measurement value of a microwave measurement object based on a transmitted microwave;
obtaining shape boundary information of the microwave measurement object;
selectively, with respect to an interior of an outer boundary determined from the obtained shape boundary information of the object, changing a distribution of electrical characteristics of an image reconstruction area mesh that is based on the microwave measurement value; and
performing an image reconstruction based on the selectively changed distribution of electrical characteristics of the image reconstruction area mesh.

11. The method of claim 10, wherein the obtaining of the shape boundary information comprises receiving the shape boundary information from a user or obtaining the shape boundary information through a controller controlled measurement of the shape boundary information of the object.

12. The method of claim 10, wherein the selective changing of the distribution of the electrical characteristics of the image reconstruction area mesh comprises:
setting the image reconstruction area mesh for a set image reconstruction area by using the microwave measurement value;
setting an outer boundary line to the image reconstruction area by using the shape boundary information; and
obtaining a microwave calculation value by calculating the microwave after setting an initial distribution for electrical characteristics to the image reconstruction area mesh.

13. The method of claim 12, further comprising calculating an error between the microwave measurement value and the microwave calculation value.

14. The method of claim 13, further comprising:
outputting the restored image when the error satisfies a preset range; and
performing again the image reconstruction by changing the distribution of electrical characteristics of the image reconstruction area mesh when the error does not satisfy the preset range.

15. The method of claim 14, wherein the performing again of the image reconstruction comprises maintaining the initial distribution of electrical characteristics for a mesh portion, of the image reconstruction area mesh, of an exterior of the outer boundary line and changing a distribution of electrical characteristics, from the corresponding initial distribution, for a mesh portion, of the image reconstruction area mesh, of an interior of the outer boundary line.

16. The method of claim 12, wherein the setting of the outer boundary line to the image reconstruction area comprises leaving a mesh portion, of image reconstruction area mesh, of an interior of the outer boundary line and removing a mesh portion, of the image reconstruction area mesh, of an exterior of the outer boundary line.

17. The method of claim 12, wherein the obtaining of the microwave calculation value comprises calculating the microwave by performing a high-speed parallel processing operation.

* * * * *